(12) United States Patent
Issa et al.

(10) Patent No.: US 10,590,161 B2
(45) Date of Patent: Mar. 17, 2020

(54) ION EXCHANGE PURIFICATION OF MRNA

(71) Applicant: ModernaTX, Inc., Cambridge, MA (US)

(72) Inventors: William Joseph Issa, Roslindale, MA (US); Joseph Louis Barberio, Watertown, MA (US); John Grant Aunins, Cambridge, MA (US); Noubar B. Afeyan, Lexington, MA (US)

(73) Assignee: ModernaTX, Inc., Cambridge, MA (US)

( * ) Notice: Subject to any disclaimer, the term of this patent is extended or adjusted under 35 U.S.C. 154(b) by 465 days.

(21) Appl. No.: 14/777,320

(22) PCT Filed: Mar. 14, 2014

(86) PCT No.: PCT/US2014/029317
§ 371 (c)(1),
(2) Date: Sep. 15, 2015

(87) PCT Pub. No.: WO2014/144767
PCT Pub. Date: Sep. 18, 2014

(65) Prior Publication Data
US 2016/0024141 A1    Jan. 28, 2016

Related U.S. Application Data

(60) Provisional application No. 61/800,110, filed on Mar. 15, 2013.

(51) Int. Cl.
*C07H 21/02* (2006.01)
*C12N 15/10* (2006.01)
(Continued)

(52) U.S. Cl.
CPC .......... *C07H 21/02* (2013.01); *B01D 15/363* (2013.01); *C12N 15/101* (2013.01); *G01N 30/96* (2013.01); *G01N 2030/8827* (2013.01)

(58) Field of Classification Search
None
See application file for complete search history.

(56) References Cited

U.S. PATENT DOCUMENTS

| 4,699,717 A | 10/1987 | Riesner et al. |
| 5,057,426 A | 10/1991 | Henco et al. |

(Continued)

FOREIGN PATENT DOCUMENTS

| CA | 2028849 A1 | 9/1991 |
| CA | 2473135 A1 | 6/2003 |

(Continued)

OTHER PUBLICATIONS

"Potato spindle tuber viroid," Wikipedia, <https://en.wikipedia.org/wiki/Potato_spindle_tuber_viroid>, accessed Jan. 19, 2017 (2 pages).

(Continued)

*Primary Examiner* — Robert T. Crow
(74) *Attorney, Agent, or Firm* — Clark & Elbing LLP

(57) ABSTRACT

The current landscape for preparative chromatographic RNA purification uses reversed phase HPLC, but this technique presents many issues with process scale up and ion exchange for preparative purification has only been used for short RNAs. The invention provides preparative purification of RNA (e.g., mRNA) using ion (e.g., anion) exchange chromatography that allows for separation of longer RNAs up to 10,000 nucleotides in length via a scalable method. This method avoids problems with current techniques by using low pressure chromatography that is agreeable with existing equipment in cGMP commercial facilities, that uses aqueous-bases solutions as the mobile phase (rather than flammable of greater than 10 mg RNA/mL resin (e.g., using larger pore sorbents, >500 Angstroms, that display greater mRNA binding capacities), and that yields desired RNA salt forms for downstream formulation with no additional (Continued)

manipulation necessary (unlike ion pair reverse phase techniques).

15 Claims, 4 Drawing Sheets

(51) Int. Cl.
  *G01N 30/96* (2006.01)
  *B01D 15/36* (2006.01)
  *G01N 30/88* (2006.01)

(56) References Cited

U.S. PATENT DOCUMENTS

| | | | |
|---|---|---|---|
| 5,338,448 A * | 8/1994 | Gjerde | B01D 15/08 |
| | | | 210/198.2 |
| 5,426,180 A | 6/1995 | Kool | |
| 5,489,677 A | 2/1996 | Sanghvi et al. | |
| 5,512,439 A | 4/1996 | Hornes et al. | |
| 5,591,722 A | 1/1997 | Montgomery et al. | |
| 5,599,667 A | 2/1997 | Arnold, Jr. et al. | |
| 5,637,459 A | 6/1997 | Burke et al. | |
| 5,639,873 A | 6/1997 | Barascut et al. | |
| 5,789,578 A | 8/1998 | Burton et al. | |
| 5,808,039 A | 9/1998 | Reddy et al. | |
| 5,989,911 A | 11/1999 | Fournier et al. | |
| 6,022,715 A | 2/2000 | Merenkova et al. | |
| 6,248,268 B1 | 6/2001 | Cook | |
| 6,303,378 B1 | 10/2001 | Bridenbaugh et al. | |
| 6,423,492 B1 | 7/2002 | Harbron | |
| 6,511,832 B1 | 1/2003 | Guarino et al. | |
| 6,521,411 B2 | 2/2003 | Hecker et al. | |
| 6,642,374 B2 * | 11/2003 | Gjerde | B01D 15/366 |
| | | | 536/25.4 |
| 6,812,341 B1 | 11/2004 | Conrad | |
| 6,881,314 B1 | 4/2005 | Wang et al. | |
| 7,691,569 B2 | 4/2010 | Wohlgemuth et al. | |
| 8,093,367 B2 | 1/2012 | Kore et al. | |
| 8,664,194 B2 | 3/2014 | de Fougerolles et al. | |
| 8,680,069 B2 | 3/2014 | de Fougerolles et al. | |
| 8,691,750 B2 | 4/2014 | Constien et al. | |
| 8,710,200 B2 | 4/2014 | Schrum et al. | |
| 8,716,465 B2 | 5/2014 | Rossi et al. | |
| 8,802,438 B2 | 8/2014 | Rossi et al. | |
| 8,822,663 B2 | 9/2014 | Schrum et al. | |
| 8,883,506 B2 | 11/2014 | Rossi et al. | |
| 8,898,864 B1 | 12/2014 | Porter | |
| 8,969,353 B2 | 3/2015 | Mahon et al. | |
| 8,980,864 B2 | 3/2015 | Hoge et al. | |
| 8,999,380 B2 | 4/2015 | Bancel et al. | |
| 9,050,297 B2 | 6/2015 | Chakraborty et al. | |
| 9,061,059 B2 | 6/2015 | Chakraborty et al. | |
| 9,089,604 B2 | 7/2015 | Chakraborty et al. | |
| 9,095,552 B2 | 8/2015 | Chakraborty et al. | |
| 9,107,886 B2 | 8/2015 | Chakraborty et al. | |
| 9,114,113 B2 | 8/2015 | Chakraborty et al. | |
| 9,149,506 B2 | 10/2015 | Chakraborty et al. | |
| 9,428,535 B2 | 8/2016 | de Fougerolles et al. | |
| 9,533,047 B2 | 1/2017 | de Fougerolles et al. | |
| 9,675,668 B2 | 6/2017 | Bancel et al. | |
| 9,751,925 B2 | 9/2017 | Hoge et al. | |
| 9,803,177 B2 | 10/2017 | Rossi et al. | |
| 9,872,900 B2 | 1/2018 | Ciaramella et al. | |
| 10,022,435 B2 | 7/2018 | Ciaramella et al. | |
| 10,064,935 B2 | 9/2018 | Ciaramella et al. | |
| 10,072,057 B2 | 9/2018 | Hoge et al. | |
| 2001/0025097 A1 | 9/2001 | Sheridan et al. | |
| 2002/0001812 A1 | 1/2002 | Smith et al. | |
| 2002/0016450 A1 | 2/2002 | Laugharn et al. | |
| 2002/0114784 A1 | 8/2002 | Li et al. | |
| 2002/0130430 A1 | 9/2002 | Castor | |
| 2002/0153312 A1 | 10/2002 | Gjerde et al. | |
| 2003/0120035 A1 | 6/2003 | Gao et al. | |
| 2003/0170810 A1 | 9/2003 | Vedadi et al. | |
| 2003/0170876 A1 | 9/2003 | Widner et al. | |
| 2003/0170891 A1 | 9/2003 | McSwiggen | |
| 2003/0180754 A1 * | 9/2003 | Bergholtz | C07H 21/00 |
| | | | 506/3 |
| 2003/0180779 A1 | 9/2003 | Lofton-Day et al. | |
| 2004/0038278 A1 | 2/2004 | Tzertzinis et al. | |
| 2004/0142433 A1 | 7/2004 | Padgett et al. | |
| 2004/0220127 A1 | 11/2004 | Sternberg et al. | |
| 2004/0224425 A1 | 11/2004 | Gjerde et al. | |
| 2004/0259097 A1 | 12/2004 | De Backer et al. | |
| 2005/0003496 A1 | 1/2005 | McGall et al. | |
| 2005/0053942 A1 | 3/2005 | Kauppinen et al. | |
| 2005/0130196 A1 | 6/2005 | Hofstadler et al. | |
| 2005/0171333 A1 * | 8/2005 | Paulsen | C07H 21/00 |
| | | | 530/300 |
| 2006/0003371 A1 | 1/2006 | Russell et al. | |
| 2006/0058266 A1 | 3/2006 | Manoharan et al. | |
| 2006/0121441 A1 | 6/2006 | Spira | |
| 2006/0223081 A1 | 10/2006 | Jarrell et al. | |
| 2007/0020678 A1 | 1/2007 | Ault-Riche et al. | |
| 2007/0037148 A1 | 2/2007 | Fong et al. | |
| 2007/0037770 A1 | 2/2007 | Gryaznov et al. | |
| 2007/0244062 A1 | 10/2007 | Laux et al. | |
| 2007/0281336 A1 | 12/2007 | Jendrisak et al. | |
| 2008/0076910 A1 | 3/2008 | Takkellapati et al. | |
| 2008/0139801 A1 * | 6/2008 | Umansky | C12N 15/101 |
| | | | 536/25.41 |
| 2008/0171711 A1 | 7/2008 | Hoerr et al. | |
| 2008/0274463 A1 | 11/2008 | Chen et al. | |
| 2008/0311140 A1 | 12/2008 | Lee et al. | |
| 2009/0192303 A1 | 7/2009 | Skagestad | |
| 2009/0215125 A1 * | 8/2009 | Reed | B01L 3/5027 |
| | | | 435/91.2 |
| 2009/0264511 A1 | 10/2009 | de Fougerolles et al. | |
| 2009/0286852 A1 | 11/2009 | Kariko et al. | |
| 2010/0015232 A1 | 1/2010 | Besenbacher et al. | |
| 2010/0047261 A1 | 2/2010 | Hoerr et al. | |
| 2010/0048883 A1 | 2/2010 | Ketterer et al. | |
| 2010/0178272 A1 | 7/2010 | Hartmann et al. | |
| 2010/0183639 A1 | 7/2010 | Uhlmann et al. | |
| 2010/0255574 A1 | 10/2010 | Rosen et al. | |
| 2010/0261228 A1 | 10/2010 | Gharib et al. | |
| 2010/0261231 A1 | 10/2010 | Kore et al. | |
| 2010/0317532 A1 | 12/2010 | Liu et al. | |
| 2011/0130440 A1 | 6/2011 | Manoharan et al. | |
| 2011/0143397 A1 | 6/2011 | Kariko et al. | |
| 2011/0218170 A1 | 9/2011 | Thottassery et al. | |
| 2011/0244026 A1 | 10/2011 | Guild et al. | |
| 2011/0281938 A1 | 11/2011 | Schaub et al. | |
| 2011/0319506 A1 | 12/2011 | Erbacher et al. | |
| 2012/0046346 A1 | 2/2012 | Rossi et al. | |
| 2012/0100136 A1 | 4/2012 | Patel et al. | |
| 2012/0129261 A1 | 5/2012 | Eberwine et al. | |
| 2012/0251618 A1 | 10/2012 | Schrum et al. | |
| 2013/0046084 A1 | 2/2013 | Brown et al. | |
| 2013/0052721 A1 | 2/2013 | Hollander et al. | |
| 2013/0058894 A1 | 3/2013 | Maldonado et al. | |
| 2013/0115272 A1 | 5/2013 | de Fougerolles et al. | |
| 2013/0115274 A1 | 5/2013 | Knopov et al. | |
| 2013/0123481 A1 | 5/2013 | de Fougerolles et al. | |
| 2013/0156849 A1 | 6/2013 | de Fougerolles et al. | |
| 2013/0165504 A1 | 6/2013 | Bancel et al. | |
| 2013/0197068 A1 | 8/2013 | Kariko et al. | |
| 2013/0203115 A1 | 8/2013 | Schrum et al. | |
| 2013/0244282 A1 | 9/2013 | Schrum et al. | |
| 2013/0245103 A1 | 9/2013 | de Fougerolles et al. | |
| 2013/0245105 A1 | 9/2013 | de Fougerolles et al. | |
| 2013/0245106 A1 | 9/2013 | de Fougerolles et al. | |
| 2013/0251618 A1 | 9/2013 | Li et al. | |
| 2013/0259923 A1 | 10/2013 | Bancel et al. | |
| 2013/0259924 A1 | 10/2013 | Bancel et al. | |
| 2014/0010861 A1 | 1/2014 | Bancel et al. | |
| 2014/0105964 A1 | 4/2014 | Bancel et al. | |
| 2014/0105966 A1 | 4/2014 | Bancel et al. | |
| 2014/0147454 A1 | 5/2014 | Chakraborty et al. | |
| 2014/0200261 A1 | 7/2014 | Hoge et al. | |
| 2014/0206752 A1 | 7/2014 | Afeyan et al. | |
| 2014/0206852 A1 | 7/2014 | Hoge et al. | |
| 2014/0243399 A1 | 8/2014 | Schrum et al. | |
| 2014/0275227 A1 | 9/2014 | Hoge et al. | |

(56) References Cited

U.S. PATENT DOCUMENTS

| | | | |
|---|---|---|---|
| 2014/0343129 A1 | 11/2014 | de Fougerolles et al. |
| 2014/0371302 A1 | 12/2014 | Afeyan et al. |
| 2015/0005372 A1 | 1/2015 | Hoge et al. |
| 2015/0017211 A1 | 1/2015 | de Fougerolles et al. |
| 2015/0030576 A1 | 1/2015 | Bancel |
| 2015/0050354 A1 | 2/2015 | Bouchon et al. |
| 2015/0050738 A1 | 2/2015 | Ozsolak et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0105275 A1 | 4/2015 | Wong et al. |
| 2015/0111248 A1 | 4/2015 | Bancel et al. |
| 2015/0141269 A1 | 5/2015 | Soldatov et al. |
| 2015/0141499 A1 | 5/2015 | Bancel et al. |
| 2015/0166616 A1 | 6/2015 | Bancel et al. |
| 2015/0167017 A1 | 6/2015 | Roy et al. |
| 2015/0211039 A1 | 7/2015 | Wang et al. |
| 2015/0291678 A1 | 10/2015 | Rudolph et al. |
| 2015/0307542 A1 | 10/2015 | Roy et al. |
| 2016/0017313 A1 | 1/2016 | Spivak et al. |
| 2016/0024140 A1 | 1/2016 | Issa et al. |
| 2016/0024141 A1* | 1/2016 | Issa .................. C12N 15/101 536/23.1 |
| 2016/0024492 A1 | 1/2016 | Issa et al. |
| 2016/0024547 A1 | 1/2016 | Bancel et al. |
| 2016/0025630 A1 | 1/2016 | Jensen et al. |
| 2016/0032273 A1 | 2/2016 | Shahrokh et al. |
| 2016/0038612 A1 | 2/2016 | Hoge et al. |
| 2016/0177295 A1 | 6/2016 | Rudolph et al. |
| 2016/0194368 A1 | 7/2016 | Hoge et al. |
| 2016/0194625 A1 | 7/2016 | Hoge et al. |
| 2016/0237108 A1 | 8/2016 | Fraley et al. |
| 2016/0244742 A1 | 8/2016 | Linnarsson et al. |
| 2016/0326575 A1 | 11/2016 | Von Der Mulbe et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2017/0088888 A1 | 3/2017 | El-Sagheer et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | |
|---|---|---|
| EP | 0366400 A2 | 5/1990 |
| EP | 1083232 B1 | 2/2005 |
| EP | 1619254 A1 | 1/2006 |
| EP | 1383556 B9 | 3/2008 |
| EP | 1831160 B1 | 6/2010 |
| EP | 2092064 B1 | 9/2010 |
| EP | 2377938 A1 | 10/2011 |
| EP | 2484770 A1 | 8/2012 |
| EP | 2188379 B1 | 1/2013 |
| EP | 2548960 A1 | 1/2013 |
| JP | 2011-130725 A | 7/2011 |
| RU | 2540017 C2 | 1/2015 |
| WO | WO-91/05058 A1 | 4/1991 |
| WO | WO-93/03052 A1 | 2/1993 |
| WO | WO-93/13121 A1 | 7/1993 |
| WO | WO-97/07825 A1 | 3/1997 |
| WO | WO-01/55306 A2 | 8/2001 |
| WO | WO-01/81566 A2 | 11/2001 |
| WO | WO-02/44399 A2 | 6/2002 |
| WO | WO-02/098443 A2 | 12/2002 |
| WO | WO-03/039523 A2 | 5/2003 |
| WO | WO-03/051881 A1 | 6/2003 |
| WO | WO-2004/020575 A2 | 3/2004 |
| WO | WO-2004/064782 A2 | 8/2004 |
| WO | WO-2005/058933 A1 | 6/2005 |
| WO | WO-2006/015445 A1 | 2/2006 |
| WO | WO-2007/024708 A2 | 3/2007 |
| WO | WO-2007/024798 A2 | 3/2007 |
| WO | WO-2007/089607 A2 | 8/2007 |
| WO | WO-2007/120863 A2 | 10/2007 |
| WO | WO-2008/039669 A1 | 4/2008 |
| WO | WO-2008/045505 A2 | 4/2008 |
| WO | WO-2008/083949 A2 | 7/2008 |
| WO | WO-2008/120016 A1 | 10/2008 |
| WO | WO-2009/042971 A2 | 4/2009 |
| WO | WO-2009/051451 A2 | 4/2009 |
| WO | WO-2009/127060 A1 | 10/2009 |
| WO | WO-2009/127230 A1 | 10/2009 |
| WO | WO-2009/147519 A1 | 12/2009 |
| WO | WO-2009/149253 A2 | 12/2009 |
| WO | WO-2010/014895 A2 | 2/2010 |
| WO | WO-2010/017510 A1 | 2/2010 |
| WO | WO-2010/054401 A1 | 5/2010 |
| WO | WO-2010/109289 A1 | 9/2010 |
| WO | WO-2010/144740 A1 | 12/2010 |
| WO | WO-2011/005850 A1 | 1/2011 |
| WO | WO-2011/012316 A3 | 2/2011 |
| WO | WO-2011/068810 A1 | 6/2011 |
| WO | WO-2011/071931 A2 | 6/2011 |
| WO | WO-2011/127933 A1 | 10/2011 |
| WO | WO-2011/130624 A2 | 10/2011 |
| WO | WO-2011/133868 A2 | 10/2011 |
| WO | WO-2011/140627 A1 | 11/2011 |
| WO | WO-2012/019168 A2 | 2/2012 |
| WO | WO-2012/135805 A2 | 10/2012 |
| WO | WO-2012/138530 A1 | 10/2012 |
| WO | WO-2012/158736 A1 | 11/2012 |
| WO | WO-2012/164565 A1 | 12/2012 |
| WO | WO-2013/039857 A1 | 3/2013 |
| WO | WO-2013/039861 A1 | 3/2013 |
| WO | WO-2013/045434 A1 | 4/2013 |
| WO | WO-2013/052523 A1 | 4/2013 |
| WO | WO-2013/090186 A1 | 6/2013 |
| WO | WO-2013/090294 A1 | 6/2013 |
| WO | WO-2013/090648 A1 | 6/2013 |
| WO | WO-2013/090897 A1 | 6/2013 |
| WO | WO-2013/096709 A2 | 6/2013 |
| WO | WO-2013/101690 A1 | 7/2013 |
| WO | WO-2013/113326 A1 | 8/2013 |
| WO | WO-2013/113501 A1 | 8/2013 |
| WO | WO-2013/113502 A1 | 8/2013 |
| WO | WO-2013/130161 A1 | 9/2013 |
| WO | WO-2013/151663 A1 | 10/2013 |
| WO | WO-2013/151664 A1 | 10/2013 |
| WO | WO-2013/151665 A2 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151669 A1 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/184976 A2 | 12/2013 |
| WO | WO-2013/185069 A1 | 12/2013 |
| WO | WO-2014/028429 A2 | 2/2014 |
| WO | WO-2014/081507 A1 | 5/2014 |
| WO | WO-2014/093574 A1 | 6/2014 |
| WO | WO-2014/093924 A1 | 6/2014 |
| WO | WO-2014/113089 A2 | 7/2014 |
| WO | WO-2014/144039 A1 | 9/2014 |
| WO | WO-2014/144711 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/160243 A1 | 10/2014 |
| WO | WO-2014/160284 A1 | 10/2014 |
| WO | WO-2014/164253 A1 | 10/2014 |
| WO | WO-2015/006747 A2 | 1/2015 |
| WO | WO-2015/034925 A1 | 3/2015 |

(56) References Cited

FOREIGN PATENT DOCUMENTS

| | | |
|---|---|---|
| WO | WO-2015/034928 A1 | 3/2015 |
| WO | WO-2015/038892 A1 | 3/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/051214 A1 | 4/2015 |
| WO | WO-2015/058069 A1 | 4/2015 |
| WO | WO-2015/070413 A1 | 5/2015 |
| WO | WO-2015/085318 A2 | 6/2015 |
| WO | WO-2015/089511 A2 | 6/2015 |
| WO | WO-2015/101416 A1 | 7/2015 |
| WO | WO-2015/105926 A1 | 7/2015 |
| WO | WO-2015/196118 A1 | 12/2015 |
| WO | WO-2015/196128 A2 | 12/2015 |
| WO | WO-2015/196130 A2 | 12/2015 |
| WO | WO-2016/010840 A1 | 1/2016 |
| WO | WO-2016/011222 A2 | 1/2016 |
| WO | WO-2016/011226 A1 | 1/2016 |
| WO | WO-2016/034620 A1 | 3/2016 |
| WO | WO-2016/036902 A1 | 3/2016 |
| WO | WO-2016/077125 A1 | 5/2016 |
| WO | WO-2016/118724 A1 | 7/2016 |
| WO | WO-2016/118725 A1 | 7/2016 |

OTHER PUBLICATIONS

Bynum et al., "Characterization of subcellular poly(A) RNA populations by poly(U) sepharose chromatography and discontinuous elution," Anal Biochem. 107(2):406-16 (1980).
Chen et al., "LC/MS analysis of cellular RNA reveals NAD-linked RNA," Nat Chem Biol. 5(12):879-81 (2009).
Colpan et al., "Large-scale purification of viroid RNA using Cs2SO4 gradient centrifugation and high-performance liquid chromatography," Anal Biochem. 131(1):257-65 (1983).
Extended European Search Report for European Application No. 14763477.8, dated Feb. 1, 2017 (16 pages).
Hamaguchi et al., "Direct reverse transcription-PCR on oligo(dT)-immobilized polypropylene microplates after capturing total mRNA from crude cell lysates," Clin Chem. 44(11):2256-63 (1998).
International Preliminary Report on Patentability and Written Opinion for International Patent Application No. PCT/US2014/029317, dated Sep. 15, 2015 (6 pages).
International Search Report for International Patent Application No. PCT/US2014/029317, dated Aug. 13, 2014 (3 pages).
Jakobsen et al., "Direct mRNA Isolation Using Magnetic Oligo (dT) Beads: A Protocol for All Types of Cell Cultures, Animal and Plant Tissues," Advances in Biomagnetic Separation. ed. Uhlén et al., Eaton Publishing, 61-71 (1994) (15 pages).
Karikó et al., "Incorporation of pseudouridine into mRNA yields superior nonimmunogenic vector with increased translational capacity and biological stability." Mol Ther. 16(11):1833-40 (2008).
Karikó et al., "mRNA is an endogenous ligand for Toll-like receptor 3," J Biol Chem. 279(13): 12542-50 (2004).
Karikó et al., "Suppression of RNA recognition by Toll-like receptors: the impact of nucleoside modification and the evolutionary origin of RNA," Immunity. 23(2):165-75 (2005).
Kazantsev et al., "Crystal structure of a bacterial ribonuclease P RNA," Proc Natl Acad Sci U.S.A. 102(38):13392-7 (2005).
Mészáros et al., "Subtractive hybridization strategy using paramagnetic oligo(dT) beads and PCR," Biotechniques 20(3):413-9 (1996).
Shimelis et al., "Nuclease P1 digestion/high-performance liquid chromatography, a practical method for DNA quantitation," J Chromatogr A. 1117(2):132-6 (2006).
Slater, Chapter 16: The Purification of Poly(A)-Containing RNA by Affinity Chromatography. Methods in Molecular Biology. ed. Walker, Springer Verlag, 117-20 (1985).
Smith et al., "Purification of polynucleotide phosphorylase by affinity chromatography and some properties of the purified enzymes," Nucleic Acids Res. 1(12):1763-73 (1974).
St. Claire, "Positive ion electrospray ionization tandem mass spectrometry coupled to ion-pairing high-performance liquid chromatography with a phosphate buffer for the quantitative analysis of intracellular nucleotides," Rapid Commun Mass Spectrom. 14(17):1625-34 (2000).
Vomelová et al., "Methods of RNA purification. All ways (should) lead to Rome," Folia Biol (Praha) 55(6):243-51 (2009).
Applied Biosystems, DNA Synthesizer Model 380B, Version 1.1 User's Manual, 2001 (327 pages).
Aviv et al., "Purification of Biologically Active Globin Messenger RNA by Chromatography on Oligothymidylic acid-Cellulose," Proc Nat Acad Sci USA 69(6):1408-1412 (1972).
Diebold et al., "Nucleic acid agonists for Toll-like receptor 7 are defined by the presence of uridine ribonucleotides," Eur J Immunol. 36(12):3256-67 (2006).
Gilham, "The Synthesis of Polynucleotide-Celluloses and Their Use in the Fractionation of Polynucleotides," J Am Chem Soc 86(22):4982-4985 (1964).
Gustafsson et al., "Codon bias and heterologous protein expression," Trends Biotechnol. 22(7):346-353 (2004).
Henke et al., "microRNA-122 stimulates translation of hepatitis C virus RNA," EMBO J. 27(24):3300-10 (2008).
International Search Report and Written Opinion for International Application No. PCT/US2017/033377, dated Jul. 28, 2017 (20 pages).
Li et al., "Effects of chemically modified messenger RNA on protein expression," Bioconjug Chem. 27(3):849-53 (2016).
Loomis et al., "Strategies for modulating innate immune activation and protein production of in vitro transcribed mRNAs," J Mater Chem B. 4(9):1619-32 (2016).
Moretti et al., "Mechanism of translational regulation by miR-2 from sites in the 5' untranslated region or the open reading frame," RNA. 16(12):2493-502 (2010).
Motorin, "RNA modification," eLS. John Wiley & Sons, DOI:10.1002/9780470015902.a0000528.pub3 (2015) (18 pages).
Nakazato et al., "Purification of messenger RNA and heterogeneous nuclear RNA containing poly(A) sequences," Methods Enzymol. 29:431-443 (1974).
Nielsen et al., "An mRNA is capped by a 2',5' lariat catalyzed by a group I-like ribozyme," Science. 309(5740):1584-7 (2005).
Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).
Quabius et al., "Synthetic mRNAs for manipulating cellular phenotypes: an overview," N Biotechnol. 32(1):229-35 (2015).
Rodriguez et al., "Magnetic poly (styrene/divinylbenzene/acrylic acid)-based hybrid microspheres for bio-molecular recognition," Micro Nano Lett. 6(6):349-352 (2011).
Supplementary Material for Thess et al., "Sequence-engineered mRNA Without Chemical Nucleoside Modifications Enables an Effective Protein Therapy in Large Animals," Mol Ther. 23(9):1456-64 (2015), accessed <http://www.sciencedirect.com/sdfe/arp/media/1-s2.0-S1525001616302738.mmc1-pdf>. (11 Pages).
Takita et al., "Precise sequential DNA ligation on a solid substrate: solid-based rapid sequential ligation of multiple DNA molecules," DNA Res. 20(6):583-92 (2013).
Thess et al., "Sequence-engineered mRNA Without Chemical Nucleoside Modifications Enables an Effective Protein Therapy in Large Animals," Mol Ther. 23(9):1456-64 (2015).
Virnekäs et al., "Trinucleotide phosphoramidites: ideal reagents for the synthesis of mixed oligonucleotides for random mutagenesis," Nucleic Acids Res. 22(25):5600-7 (1994).
Weissman et al., "mRNA: Fulfilling the Promise of Gene Therapy," Mol Ther. 23(9):1416-7 (2015).
Brand et al., "Biosynthesis of a Hypermodified Nucleotide in Saccharaomyces carisbergensis 17S and HeLa-Cell 18S Ribosomal Ribonucleic Acid," Biochem J 169(1):71-77 (1978) (9 pages).
Kormann et al., "Expression of therapeutic proteins after delivery of chemically modified mRNA in mice," Nat Biotechnol. 29(2):154-7 (including supplement) (2011) (6 pages).

(56) References Cited

OTHER PUBLICATIONS

RNA Modification Database Entry for 1-methylpseudouridine <https://mods.rna.albany.edu/mods/modifications/view/55>, retrieved on Feb. 26, 2019 (1 page).

* cited by examiner

ION EXCHANGE PURIFICATION OF MRNA

BACKGROUND OF THE INVENTION

Field of the Invention

The present invention relates to a method for ion exchange chromatography, and specifically ion exchange chromatography for preparative RNA transcript separations of long RNA transcripts.

Description of the Related Art

RNA transcripts have strong potential as therapeutics, but effective purification of these RNA transcripts for introduction into the body remains a problem. The current landscape for the preparative chromatographic purification of RNAs utilizes reversed phase high performance (or high pressure) liquid chromatography (RP-HPLC) performed with both porous and non-porous sorbents [1]. Use of RP-HPLC presents many issues regarding process scale up. Small-particle-sized sorbents referenced lend themselves to extremely high pressure processes unsuitable for large scale unit operations. Additionally, the use of organic/flammable solvents along with high pressure liquid handling equipment can be prohibitive for large scale manufacturing. These challenges include the introduction of USP class II residual solvents (acetonitrile and methanol) into the drug substance, the potential need for an explosion proof production facility, and the many obstacles presented by large scale, high pressure processes, including cost and availability. The addition of organic solvent during purification also requires significant additional downstream processing to ensure adequate removal of the solvent from the drug substance. Introduction of ion pair reagents (e.g., alkylammonium salts) is also problematic, since this produces salt form heterogeneity as these organic salts interact with the phosphate backbone. Additional unit operations are required to remove the ion pair reagents, obtain the desired salt form, and remove residual organic solvents. Furthermore, the binding capacity of the resins contained within in the prior art for preparative RNA purification has been shown to be less than 10 mg RNA/mL resin, and in some cases having extremely low binding capacities of less than 0.02 mg/mL, which is not viable for large scale manufacturing. [6][7] These low binding capacities lead to limited process productivity and throughput and can be cost prohibitive.

Previous work has also been performed using anion exchange chromatography as the method for preparative purification of RNA [2] [3]. While this has proven to work adequately for separations of short synthetic RNAs or RNA transcripts of 300 nucleotides in size or less, these methods have not been shown to work for longer RNAs or RNA transcripts of greater than 500 nucleotides in length. In addition, these methods use weak anion exchangers and operate under non-denaturing conditions. Purification techniques for longer RNAs and full length transcripts for use in therapeutics is desirable, preferably techniques that are scalable, reproducible, and thus usable for large scale manufacturing of therapeutics.

SUMMARY OF THE INVENTION

Ion exchange chromatography for preparative RNA transcript separations of the present invention provides a solution that allows for separations of longer RNA transcripts, including lengths of up to at least 10,000 nucleotides, which is significantly larger than has been possible in the past with ion exchange chromatography. In addition, the methods allow for separations of chemically modified RNA transcripts, which was also not possible with past techniques.

Unlike prior RP-HPLC methods, since the methods of the present invention are low pressure chromatography methods, they are agreeable with existing equipment in cGMP commercial facilities. Aqueous based solutions can be used as the mobile phase for the purification step, thereby avoiding problems with flammable organic solvents. Sorbents used with the present invention have larger pore sizes (e.g., greater than 500 Angstroms), which display greater RNA binding capacities, such as binding capacities of greater than, but not limited to, 10 mg RNA/mL sorbent. Indeed, the binding capacity is approximately 1000 times or 3 orders of magnitude higher than some prior RP-HPLC methods. Counter-ion exchange of the present invention yields a desired RNA salt form for downstream therapeutic formulation with no additional manipulation necessary, including no requirement for an additional step with an ion pair reverse phase.

In addition, unlike prior anion exchange methods for purifying RNA transcripts, the present invention allows for preparative purification of chemically modified RNA transcripts and of longer RNA transcripts, including lengths up to 10,000 nucleotides. Large RNA transcripts are difficult to elute from the anion exchange sorbent due to the associated charge density of these large molecules of interest. A larger RNA molecule exhibits much stronger interactions with the anion exchange sorbent than smaller RNAs. The present invention uses various techniques (e.g., use of denaturing conditions in one or more of the ion exchange steps) to promote elution of the RNA transcript, thus making elution of longer RNA transcripts possible. For example, thermal denaturing conditions drive desorption at less aggressive conditions, such as at a lower ionic strength or a lower chaotrope concentration, etc., than are required at ambient temperature.

Thus, the ion exchange chromatography methods of the present invention are scalable, reproducible mechanisms for large scale purification of longer RNA transcripts and chemically modified RNA transcripts.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Definitions

Figure 1:
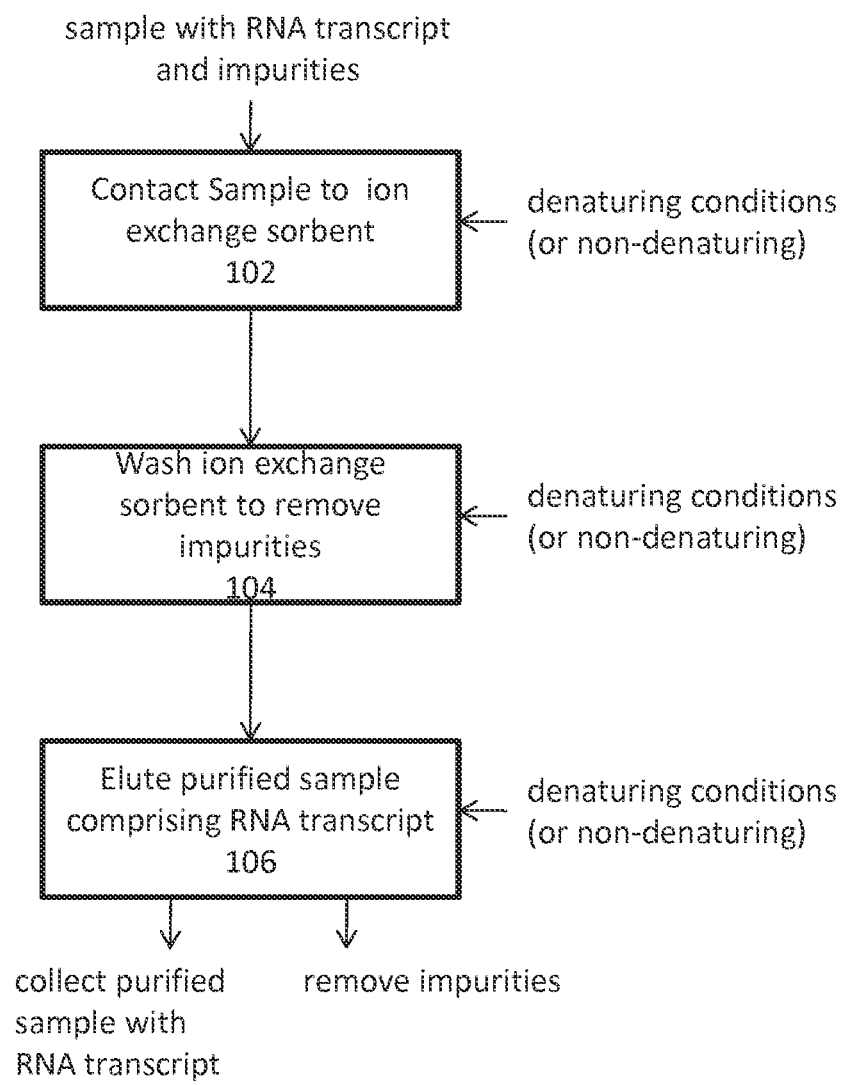
FIG. 1 is a flow chart illustrating an overview of the RNA transcript purification methods, in accordance with an embodiment of the invention.

Terms used in the claims and specification are defined as set forth below unless otherwise specified.

The term "approximately" or "about" means +/−10% of the recited value.

The terms "associated with," "conjugated," "linked," "attached," "coupled," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used.

The term "chaotropic agent" is a substance that disrupts the structure of, or denatures, biological materials or macromolecules, such as proteins and nucleic acids. A chaotropic salt is an example of such an agent.

The terms "characterize" or "characterizing," when used with regard to a polynucleotide (e.g., RNA transcript) or impurities separated using methods described herein, refers to determining information about the polynucleotide or one or more of the impurities, such as determining information about or quantifying charge density or heterogeneity, size or structural heterogeneity, physical-chemical stability, structural isoforms, among other aspects associated with the polynucleotide or one or more of the impurities.

The term "denaturing conditions" refers to conditions that cause a biological material or macromolecule, such as a nucleic acid or protein, to lose a structure (e.g., a tertiary structure or secondary structure) that is present in its native state, by application of some external stress or compound, such as a chaotropic agent, a concentrated inorganic salt, an organic solvent, or heat (thermal denaturing conditions). "Non-denaturing conditions" are conditions that do not cause the biological material to lose this structure. "Partially denaturing conditions" are conditions that cause the biological material to lose at least a portion of this structure.

The term "DNA template" refers to a polynucleotide template for RNA polymerase. Typically a DNA template includes the sequence for a gene of interest operably linked to a RNA polymerase promoter sequence.

The term "eluent" refers to a carrier portion of the mobile phase, such as a solvent or mixture of solvents with which a sample can be delivered in a chromatographic process.

The term "eluate" refers to the material that emerges from or is eluted from a chromatographic process.

The term "impurities" or "contaminants" refers to unwanted components, material defilement, admixture, byproducts of a reaction, or imperfections in a sample. For example, impurities removed in a purification of a long or full-length RNA transcript can include short transcripts, DNA template utilized during in vitro transcription, hybridized nucleic acid impurities, and process related impurities (e.g., enzymes, endotoxin, nucleotides, small molecules, etc.).

The term "in vitro" refers to events that occur in an artificial environment, e.g., in a test tube or reaction vessel, in cell culture, in a Petri dish, etc., rather than within an organism (e.g., animal, plant, or microbe).

The term "mobile phase" refers to a phase or portion that moves in a chromatographic method, such as by passing through a column, and it includes the sample and the eluent.

The term "modified" or "chemically modified" refers to a changed state or structure of a molecule of the invention. Molecules may be modified in many ways including chemically, structurally, and functionally. In one embodiment, the RNA transcripts of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

The term "native" or "naturally occurring" as used throughout the specification in connection with biological materials such as polypeptides, nucleic acids, host cells, and the like, refers to materials which are found in nature or a form of the materials that is found in nature.

The term "polynucleotide" is interchangeable with nucleic acid, and includes any compound and/or substance that comprise a polymer of nucleotides. RNA transcripts produced by the method of the invention and DNA templates used in the methods of the invention are polynucleotides. Exemplary polynucleotides include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

The terms "purify," "purified," "purification" means to be or make substantially pure or clear from unwanted components, material defilement, admixture or imperfection. The term "RNA transcript" refers to a ribonucleic acid produced by an in vitro transcription reaction using a DNA template and an RNA polymerase. As described in more detail below, an RNA transcript typically includes the coding sequence for a gene of interest and a poly A tail. RNA transcript includes an mRNA. The RNA transcript can include modifications, e.g., modified nucleotides. As used herein, the term RNA transcript includes and is interchangeable with mRNA, modified mRNA "mmRNA" or modified mRNA, and primary construct.

The term "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 70%, 75%, 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "sample" refers to a subset of the tissues, cells or component parts of an organism, such as nucleic acids, proteins, body fluids, etc. or a homogenate, lysate or extract prepared from a whole organism or a subset of its tissues, cells or component parts, or a fraction or portion thereof. A sample further refers to a medium or phase or preparation thereof, such as a nutrient broth or gel or other delivery agent, which may contain cellular components, such as proteins or nucleic acid molecules.

The terms "scalable" or "large scale" when used in terms of processes or methods that are scalable or for large scale use refer to processes or methods that are readily usable or readily adaptable for use in a standard cGMP large scale production or manufacturing facility for generating compounds, such as drugs or therapeutics.

The term "sorbent" refers to a material to which one or more components of the sample (e.g., the RNA transcript and/or impurities) adsorb.

The term "solid phase media" or "stationary phase" refers to the phase or portion that is fixed in place or stationary in a chromatographic process, such as a solid material within a column through which the mobile phase passes.

The term "therapeutic agent" or "therapeutic" refers to any agent that, when administered to a subject, has a therapeutic, diagnostic, and/or prophylactic effect and/or elicits a desired biological and/or pharmacological effect.

Those skilled in the art will recognize, or be able to ascertain using no more than routine experimentation, many equivalents to the specific embodiments in accordance with the invention described herein. The scope of the present invention is not intended to be limited to the above, but rather is as set forth in the appended claims.

It must be noted that, as used in the specification and the appended claims, the singular forms "a," "an" and "the" include plural referents unless the context clearly dictates otherwise.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Standard techniques can be used for recombinant DNA, oligonucleotide synthesis, and tissue culture and transformation (e.g., electroporation, lipofection). Enzymatic reactions, purification techniques and other techniques, such as RNA synthesis, can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Methods of the Invention

It is of great interest in the fields of therapeutics, diagnostics, reagents and for biological assays to be able to deliver a nucleic acid, e.g., a ribonucleic acid (RNA) transcript inside a cell, whether in vitro, in vivo, in situ or ex vivo, such as to cause intracellular translation of the nucleic acid and production of an encoded polypeptide of interest. Examples of modified RNA, e.g., RNA transcripts, e.g., mRNA, are disclosed in the following which is incorporated by reference for all purposes: U.S. patent application Ser. No. 13/791,922, "MODIFIED POLYNUCLEOTIDES FOR THE PRODUCTION OF BIOLOGICS AND PROTEINS ASSOCIATED WITH HUMAN DISEASE," filed Mar. 9, 2013.

Practice of the method of the present invention purifies RNA transcripts on a preparative scale by ion exchange chromatography, such as by anion exchange (AEX) chromatography. AEX chromatography is a method of purification that leverages ionic interaction between positively charged sorbents and negatively charged molecules. AEX sorbents typically include a charged functional group crosslinked to solid phase media. There are two categories of anion exchange media, "strong" and "weak" exchangers or exchange groups. The classification of strong and weak anion exchangers refers to the ionization of the ability of the charged functional groups to ionize in response to a change in pH. Strong anion exchangers maintain the same charge density over a broad pH range (e.g. a pH range from 2 to 12, from 2 to 11, from 3 to 9), while weak anion exchangers exhibit charge densities which vary with changes in pH. As a result, the binding capacity and selectivity of weak exchangers can be manipulated by the pH of the mobile phase. Anion exchange sorbents or resins facilitate RNA capture due to the interaction with the negatively charged phosphate backbone of the RNA transcript, providing an effective mode of separation.

The AEX chromatography for preparative RNA transcript separations of the present invention allows for separations of longer RNA transcripts than has been possible in the past. In some embodiments, the method allows for purification of RNA transcripts of 300 to 10,000 nucleotides in length, including purification of RNA transcripts in the following ranges: 500 to 10,000 nucleotides, 550 to 10,000 nucleotides, 600 to 10,000 nucleotides, 700 to 10,000 nucleotides, 800 to 10,000 nucleotides, 900 to 10,000 nucleotides, 1,000 to 10,000 nucleotides, 5,000 to 10,000 nucleotides, or any ranges or values within these. In some embodiments, the method allows for purification of RNA transcripts in preferred ranges of 700 to 3,000 nucleotides, 700 to 4,000, 800 to 4,000, or 800 to 2,000 nucleotides in length. This is significantly larger than has been possible in the past with ion exchange chromatography. In some embodiments, the RNA transcript is a full length transcript. As used herein, the term "large RNA transcript" or "long RNA transcript" refers to any RNA transcript falling within any of the ranges described here, including a full length transcript.

The AEX chromatography for preparative RNA transcript separations of the present invention allows for separations of native RNA transcripts or RNA transcripts that are chemically modified. Various modifications are made to RNA transcripts used as therapeutics to, for example, avoid eliciting an immune response to the therapeutic. Examples of chemical modifications that might be made to RNA transcripts are provided in U.S. patent application Ser. No. 13/791,922, "MODIFIED POLYNUCLEOTIDES FOR THE PRODUCTION OF BIOLOGICS AND PROTEINS ASSOCIATED WITH HUMAN DISEASE," filed Mar. 9, 2013, which is incorporated by reference for all purposes. These chemically modified RNA transcripts can be purified using the methods of the present invention.

The methods of the present invention are also highly scalable and reproducible. Since the methods are low pressure chromatography methods, they are agreeable with existing equipment in cGMP commercial facilities. They do not require special explosion proof production facilities and equipment that can be required for RP-HPLC techniques involving small particle sized sorbents (e.g., 8-25 µm) that lend themselves to extremely high pressure processes unsuitable for large scale unit operations. Aqueous based solutions can be used as the mobile phase for the purification step, thereby avoiding problems with flammable organic solvents that can also be prohibitive for large scale manufacturing. Sorbents used with the present invention have larger pore sizes (e.g., greater than 500 Angstroms), which display greater RNA binding capacities than RP-HPLC (e.g., binding capacities of greater than, but not limited to, 10 mg RNA/mL sorbent), thus providing better process productivity and throughput. Counter-ion exchange of the present invention yields a desired RNA salt form for downstream therapeutic formulation with no additional manipulation necessary. Thus, there is no requirement for an additional step with an ion pair reverse phase that can be required with the addition of organic solvent, which requires significant additional downstream processing to ensure its adequate removal from the drug substance.

FIG. 1 is a flowchart illustrating the method of ion exchange chromatography, according to one embodiment of the invention. In this embodiment, the process comprises a method for purifying an RNA transcript from a sample comprising the RNA transcript and impurities. The RNA transcript can be a large RNA transcript or a chemically modified RNA transcript. The method includes a step of contacting 102 (or loading or delivering) the sample to an ion exchange sorbent. The sample can be delivered via a mobile phase (e.g., a loading buffer or other mobile phase) including an eluent selected to effect separation of the components of the sample. The mobile compositions can include any of the Hofmeister ions, salts (e.g., chloride, bromide, citrate, iodide, sulfate, phosphate, perchlorate, etc.), among other mobile phase constituents. Mobile phase additives/modifiers can include organic materials, such as ethanol, acetonitrile, isopropanol (IPA), DMSO, surfactant modifiers (e.g., polyethylene glycol), etc. In some embodiments, the sample or mobile phase comprises an aqueous-based solution.

The ion exchange sorbent can comprise a positively-charged functional group linked to solid phase media. The ion exchange sorbent used can have a binding capacity of greater than 10 mg RNA transcript/mL sorbent, or greater than 12, 15, 20, 25, 30, 35, 40, 45, 50, 55, 60, 100 mg RNA/mL sorbent or higher, or any value or fractional value in between, or any range including or within these numbers. The sorbent can also have smaller binding capacities of 1 to 10 mg RNA transcript/mL sorbent. In some embodiments the ion exchange sorbent is a porous media. A variety of different particle and pore sizes can be used. Particle sizes can include standard sizes used in chromatography methods, including sizes in the range of less than 1 µm or 1 to 500 µm (e.g., 5, 10, 20, 50, 75, 100, 150 . . . µm), or any number or fractional number in between, or any range including or within these numbers. Larger or smaller sizes can also be used. Particles can include small silica beads or other types of particles. Pore sizes can include sizes that are greater than 500 Angstroms, or greater than or equal to 600, 700, 800, 900, 1,000, 2000, 4000, or 8000 Angstroms, or any number or fractional number in between, or any range including or within these numbers. Smaller pore sizes can also be used, such as 1 to 500 Angstroms. The ion exchange sorbent can be poly styrene divinylbenzene, polymethacrylate, cross-linked agarose, silica, or allyl dextran with N—N-bis acrylamide, among a variety of other sorbents. The ion exchange sorbent can also be a non-porous media, such as a monolithic column. In some embodiments, membrane-based ion exchangers are used, such as MILLIPORE CHROMASORB™ or SARTORIUS SARTOBIND™. In some embodiments, a mixed mode or combination of ion exchangers can be used. As explained above, the ion exchange sorbent or resin can be strong or weak. The term weak resins includes resins that have a low affinity for polypeptides and a high affinity for polynucleotides, e.g., RNA transcripts. The term weak resins also includes resins that have a low affinity for polypeptides and a low affinity for polynucleotides, e.g., RNA transcripts.

A variety of different positively-charged functional groups can be included in the ion exchange sorbent, such as a quaternary amine, a polyethylenimine, a diethylaminomethyl, and a dimethylaminopropyl. In some embodiments, the solid phase media is a strong anion exchanger (e.g., maintain a positive charge over a broad pH range, such as over pH 3 to pH 9), such as a quaternary amine. Though in other embodiments a weak anion exchanger can be used, such as a polyethylenimine, a diethylaminomethyl, a dimethylaminopropyl, or a polyallylamine.

The RNA transcript in the sample binds the positively-charged functional group of the ion exchange sorbent. The impurities may bind the ion exchange sorbent (e.g., a functional group of the sorbent) upon loading, and so be captured by the sorbent. The impurities or at least a portion of the impurities may also pass through the ion exchange sorbent upon loading.

Loading conditions for the AEX chromatography can be performed under denaturing conditions, partially denaturing conditions, or non-denaturing conditions. The denaturing conditions can include conditions that cause denaturing of the RNA transcript due to temperature, chaotropic agents (including salts), organic agents, among other mechanisms for denaturing. With thermal denaturing conditions, an elevated temperature can be applied. The elevated temperature can be one that is sufficient to denature intramolecular hydrogen bonds, to denature intermolecular bonding (e.g., in which the RNA transcript associates with other RNA transcripts to create higher order structures or multimers), or to cause a change in or loss of secondary tertiary, or quaternary structure. For example, the temperature or thermal denaturing conditions can include a temperature of 35 to 85 degrees Celsius, 55 to 75 degrees Celsius, or of another range within those ranges. Similarly, higher or lower temperatures can be used as appropriate to cause the desired level of denaturing. In one embodiment, the elevated temperature is a temperature of 65 degrees Celsius. The temperature or thermal denaturing conditions can also be dependent on the identity of the RNA transcript, such that different temperatures are used for different RNA transcripts or types of RNA transcripts. In some embodiments, the sample or the mobile phase (or a component of the mobile phase) is pre-incubated (before loading) at an elevated temperature sufficient to denature intramolecular hydrogen bonds. In addition, the denaturing conditions can be created by heating/incubating or placing a jacket around the column used for the purification. The denaturing conditions can also include using chaotropic agents, such as lithium perchlorate and other perchlorate salts, guanidinium chloride and other guanidinium salts, urea, butanol, ethanol, lithium acetate, magnesium chloride, phenol, propanol, sodium dodecly sulfate, thiourea, and various detergents, among others. [4][5] The denaturing conditions can further include organic denaturing agents, such as dimethyl sulfoxide (DMSO), acetonitrile, ethanol, and glyoxal. In addition, the denaturing conditions can include a combination of two or more of these types of denaturing conditions. The denaturing conditions can be applied during one or more of the steps of the method shown in FIG. 1, including during the contacting 102, washing 104, and/or eluting 106 steps. Similarly, non-denaturing conditions or partially denaturing conditions can be used during any one or more of the steps. Any one or more of the steps can be performed at an elevated temperature or at ambient temperature, with or without chaotropic or organic agents, and so forth.

Though not necessarily included in all embodiments, in some embodiments the process can also include a step of washing 104 the ion exchange sorbent, for example with a washing buffer. In some cases, the wash buffer is a loading or elution buffer, or some gradient percentage of loading or elution buffer. Where the impurities were captured by the ion exchange sorbent, the washing step can cause the impurities to be released and washed from the ion exchange sorbent as eluate. Where the impurities or a portion of the impurities passed through the ion exchange sorbent at the loading step, the washing can cause any remaining portion of the impurities to pass through the ion exchange sorbent. The washing step can be performed under any of the denaturing conditions described above, or under partially denaturing or non-denaturing conditions. In one example, the wash step is performed with a low salt buffer (e.g., a salt concentration of approximately 150 mM NaCl (7.5% Buffer B1), as described in the Examples section below) under thermal denaturing conditions. The washing step can be performed at an elevated temperature or can also be performed at ambient temperature. Wash buffers used can include Tris, 4-(2-hydroxyethyl)-1-piperazineethanesulfonic acid (HEPES), phosphate, among others. The wash buffer is selected to cause the captured impurities to be released from the sorbent or to cause any remaining impurities to be washed from the sorbent where the impurities generally passed through during loading. In one embodiment, the washing step is performed under conditions that comprise a lower ionic strength than is used in the eluting step and a higher ionic strength than is used during the contacting step.

The process can further include a step of eluting 106 from the ion exchange sorbent a purified sample comprising the RNA transcript. In some embodiments, this is performed with an elution buffer that is delivered across the ion exchange sorbent. In other embodiments, the eluting 106 step is simply the collection of materials that passed across the ion exchange sorbent, such as materials passed during the contacting 102 step or during a washing 104 step. The eluting step can be performed under any of the denaturing conditions described above, or under partially denaturing or non-denaturing conditions. For example, the eluting can occur under thermal denaturing conditions (elevated heat) or at ambient temperature.

In some embodiments, the eluting 106 step or possibly the washing 104 step occur by using a gradient-based wash or elution. For example, the method can include eluting bound impurities as a gradient-based elution using a solution containing a mixture a buffer A and a buffer B, where these can be any of the buffers/mobile phase constituents described herein. An increase in percentage of buffer B as a function of time allows fractionating individual impurities with various retentions. Thus, different impurities that bind the sorbent to different degrees can be separated and washed or eluted using this gradient-based method. In other embodiments, the eluting 106 step or possibly the washing 104 step occur by isocratic washing or eluting. For example, the method can include isocratically eluting impurities stepwise, at discreet percentages of buffers A and B. In further embodiments, the sample is loaded or contacted 104 in a mobile phase that has a salt concentration that is sufficient to prevent binding of the sorbent by the impurities, or some other mechanism is used to prevent this binding (e.g., using a sorbent to which the impurities do not bind). In this case, at least a portion of the impurities pass through and are eluted from the ion exchange sorbent upon loading. This may or may not include a wash step to wash any remaining impurities through the sorbent. These are just some examples for designs of the method, including the contacting, washing, and eluting steps. A person of ordinary skill in the art will recognize that other designs are possible and will be able to discern the preferred impurity wash and/or elution method based on the particular purification being conducted.

In some embodiments, at least 70% of the RNA transcript in the sample is recovered in the purified sample, or at least 75%, 80%, 85%, 90%, 95%, 96%, 97%, 98%, 99%, 99.5%, 100%, and so forth, including any percentages in between and any ranges including these percentages. This purification method is able to resolve short transcripts, DNA template utilized during in vitro transcription, hybridized nucleic acid impurities, and process related impurities (e.g., enzymes, endotoxin, nucleotides, small molecules, etc.). Smaller recovery rates are also possible depending on the embodiment. The ion exchange method of the present invention can be performed as a column chromatography method, as a batch chromatography method, as a chromatography method using a membrane adsorber, etc. The method also includes a counter-ion exchange that yields the RNA transcript eluted in a salt form for downstream therapeutic formulation that does not require removal of ion pair reagents, as is typically required with RP-HPLC methods, as explained above. Counter-ions/cations involved in this counter-ion exchange can include Na+, K+, Ca++, among others.

Large RNA transcripts are difficult to elute from the separation matrix due to the associated charge density of the molecules. Large RNA transcripts exhibits much stronger interactions with the ion exchange sorbent than smaller RNA transcripts. In addition, RNAs can form into high complexity, structured macromolecules, and they have the ability to fold into many unique structures and conformations. Furthermore, RNA transcripts can associate with other RNA transcripts and form higher order structures. These phenomena may contribute to the very strong interactions with the sorbent. One mechanism for addressing this issue is to use denaturing conditions, such as thermal denaturing, which appear to drive desorption (elution step) at less aggressive conditions (lower ionic strength, less chaotrope concentration, etc. than are required for elution at ambient temperature). It is thus possible under the present invention to cause desorption to occur so the large RNA transcript can be separated from impurities by using conditions specifically designed to cause this desorption and separate large RNA transcripts and chemically modified RNA transcripts from impurities. For example, the method can be designed to any combination of denaturing conditions during the purification steps (e.g., elevated temperature during the elution step with at least one chaotropic agent), to use a strong anion exchanger, to use a low ionic strength wash buffer, and so forth. The combination of conditions can be specifically designed to provide the optimal conditions for purification of the particular RNA transcript of interest.

Another mechanism for addressing the issue with large RNA transcripts having stronger interactions with the sorbent is to use an ion exchange sorbent or resin with a charge density (e.g ion exchange capacity) that is sufficiently low enough to facilitate weak binding of the RNA transcript to the sorbent and enables that enables elution at a lower salt concentration than might be required with a sorbent having a charge density that is sufficiently high to facilitate strong binding. The ion exchange capacity is typically expressed as milliequivalents (meq)/mL of sorbent. 1 meq/mL is equal to 1 mmol of charge per mL of sorbent. In some embodiments the sorbent will have an ion exchange capacity of <0.1 meq/mL, <0.05 meq/mL, <0.025 meq/mL, <0.01 meq/mL, <0.005 meq/mL, <0.0025, or <0.0001 meq/mL. Some embodiments may be performed under denaturing conditions, others may not. Thus, again it is possible under the present invention to cause desorption to occur so the large RNA transcript can be separated from impurities.

The method for purifying the RNA transcript generates RNA transcript in a purified state. This RNA transcript can be used in a therapeutic, such as an injectable RNA transcript or mRNA for treatment of diseases. These can be formulated in pharmaceutical compositions. These compositions can comprise, in addition to the RNA transcript, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

Administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1

Dynamic Binding Capacity Determination AEX at Elevated Temperature (65° C.)

Materials:
The materials used in the experimental methods described in Example 1 include the following:
 1. RNA: GCSF encoded chemically modified mRNA (Lot 12-04-85-I) (888 ng/µL)
    a. Chemistry includes Adenosine, guanosine, 5-methylcytidine, and N-1-methylpseudouridine residues
 2. Resin: POROS® HQ 50 (LIFE TECHNOLOGIES™)
 3. FPLC: AKTA™ AVANT 150 (GE HEALTHCARE™)
 4. Mobile Phase Heater: TLC 600 Mobile Phase Heater (TIMBERLINE INSTRUMENTS™)
 5. EXPERION™ Bioanalyzer (BIORAD LABORATORIES™)
 6. 2× Sample Dilution Buffer: 100 mM Tris, 300 mM NaCl, pH 7.0
 7. Sanitization/Strip Buffer: 1 M NaOH 8. Column Storage Buffer: 20% Ethanol
9. RNase Free MILLIQ™ Water
10. AKTA™ Buffers (Line):
    a. (A1) 50 mM Tris HCl, pH 7.0
    b. (A5) 50 mM Tris HCl, 150 mM NaCl, pH 7.0
    c. (B1) 50 mM Tris HCl, 2 M NaCl, pH 7.0

Methods:

An 899 nucleotide mRNA transcript encoding GCSF protein (lot 12-04-85-I) containing adenosine, guanosine, 5-methylcytidine, and N-1-methylpseudouridine was utilized as the feedstock for the separation. A packed column of POROS® HQ resin was used as the stationary phase of the purification. The column had a diameter of 10.0 mm, a length of 2.4 cm, and a volume of 1.9 mL. Column equilibration product loading, Post Load Rinse, Wash, and Elution steps were performed at 65° C.; the elevated temperature was reached by preheating mobile phase through the mobile phase heater prior to loading on the column.

The 20% ethanol storage solution was flushed from the column with ≥5 column volumes (CVs) of Buffer A1. The resin was stripped/sanitized with ≥5 CVs of 1 M NaOH. The column was then equilibrated with Buffer A5, followed by a 1:1 mixture of Buffers A1-B1, then Buffer A5 (≥5 CVs for each step). 30 mL of GCSF modified mRNA was diluted 1:1 with sample dilution buffer. The column was then loaded with 57.6 mL of GCSF modified mRNA and post load rinsed with >20 mL of Buffer A5; the effluent was collected and pooled as the flow-through (FT) fraction. The column was washed with ≥10 CVs of Buffer A5. Elution was performed by a linear gradient of 25%-67.5% Buffer B1 over 17 minutes at a linear velocity of 300 cm/hr. 7.8 ml fractions were collected over the course of the elution. The fractions were pooled as follows:

Elution Pool A: 5.A.1-5.A.3
Elution Pool B: 5.A.4-5.B.5
Elution Pool C: 5.C.1-6.A.1

A strip step was performed with ≥5 CVs 100% Buffer B1 followed by ≥5 CVs of 1 M NaOH sanitization. The column was re-equilibrated with ≥5 CVs of Buffer A1 and stored in 20% ethanol.

Figure 2:
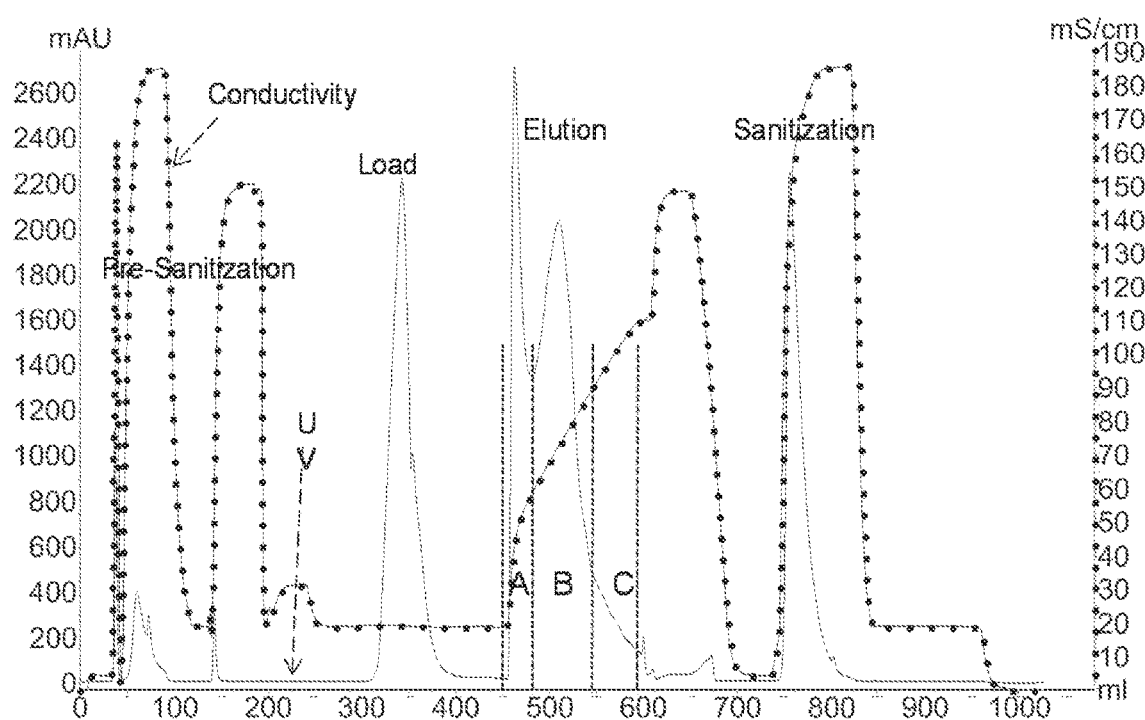
FIG. 2 is a chromatogram of an AEX separation, in accordance with an embodiment of the invention.

The pooled fractions were subjected to concentration determination by $A_{260}$. RNA integrity analysis was performed by chip based electrophoresis on the bioanalyzer, samples were diluted to ~100 ng/µL in RNase free water prior to analysis. FIG. 2 is a preparative chromatogram of the AEX separation denoting UV absorbance at 260 nm and conductivity.

The appearance of a peak due to the increase in UV absorbance at 260 nm during the load is caused by break through of unbound RNA. This break through indicates column saturation and suggests the binding capacity of the resin, under the given conditions, has been reached. The linear increase of the conductivity trace is in response to the increasing percentage of Buffer B1 during the gradient elution step. Vertical dashed lines segmenting the elution peak designate the approximate breakpoint for each of the elution pools, while the letters contained within the segments correspond to the designation of each pool. The appearance of a UV peak during the elution step demonstrates the ability of these particular conditions to both bind and elute at least a portion of the loaded material. The dynamic binding capacity of the sorbent for the given molecule of interest was observed to be 20.9 mg RNA/mL sorbent while the recovery of bound material in the elution fractions was 86.6% as shown in Table 1.

Results:

Table 1 below illustrates the results of the methods described above.

TABLE 1

Mass balance for AEX step

| Sample | Concentration (µg/mL) | Volume (mL) | Mass (µg) | Yield (%) |
|---|---|---|---|---|
| Loaded GCSF modified mRNA | 888.9 | 57.6 | 51200.6 | |
| Flow-through Pool | 85.2 | 134.3 | 11442.4 | |
| Elution Pool A | 362.7 | 23.7 | 8596.0 | 21.6 |
| Elution Pool B | 398.2 | 55.8 | 22219.6 | 55.9 |
| Elution Pool C | 74.5 | 48.5 | 3613.3 | 9.1 |
| | | | Total Yield: | 86.6 |

Dynamic Binding Capacity (mg RNA/mL sorbent) = 20.9 mg/mL

Figure 3A:
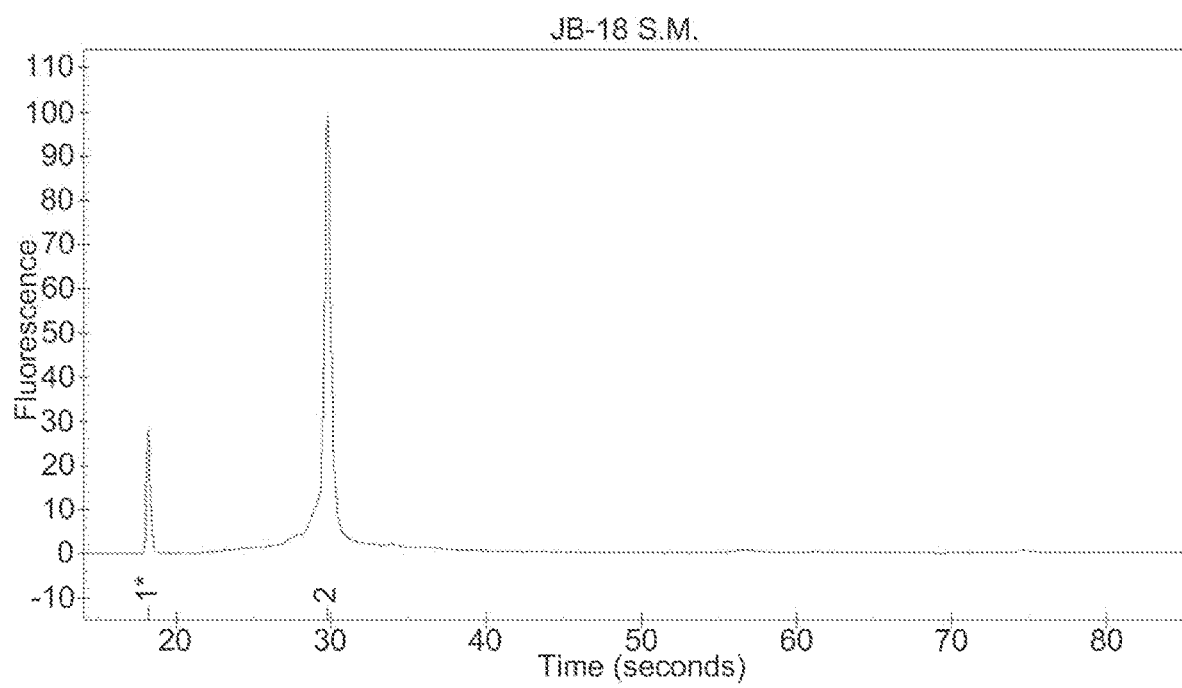
FIG. 3A is an electropherogram of AEX chromatography fractions illustrating GCSF modified mRNA diluted with 2× Sample Buffer (Load Material/Starting Material) \, in accordance with an embodiment of the invention
Figure 3B:
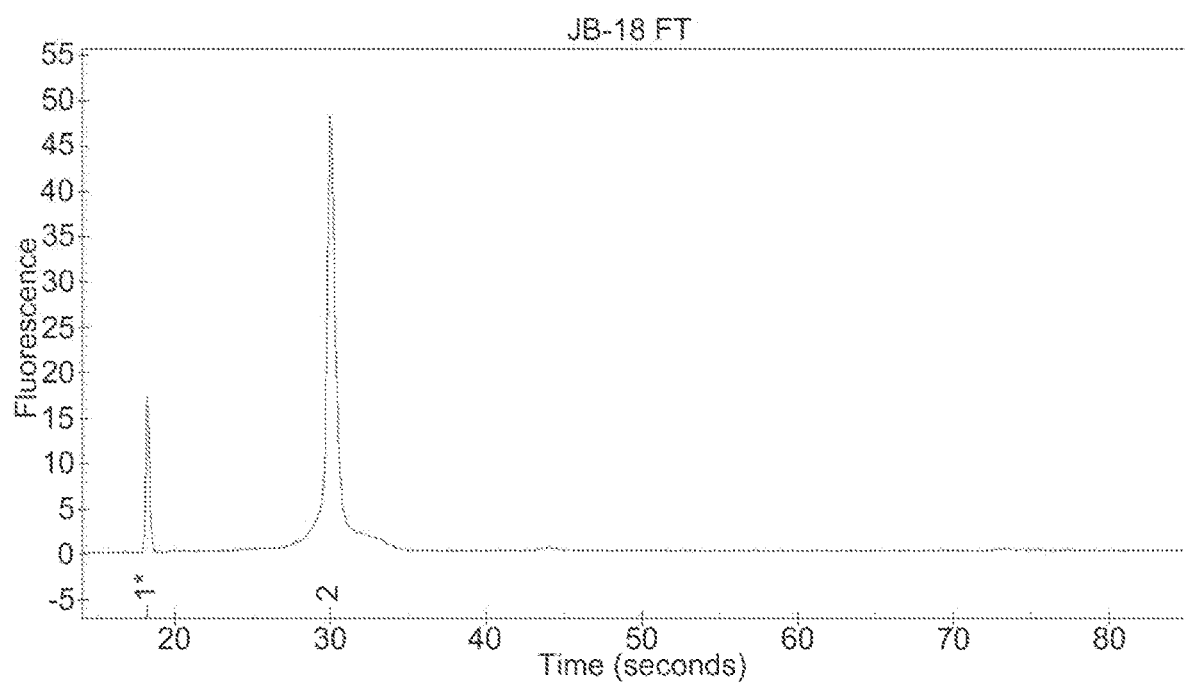
FIG. 3B is an electropherogram of AEX chromatography fractions illustrating AEX purification Flow Through Pool, in accordance with an embodiment of the invention
Figure 3C:
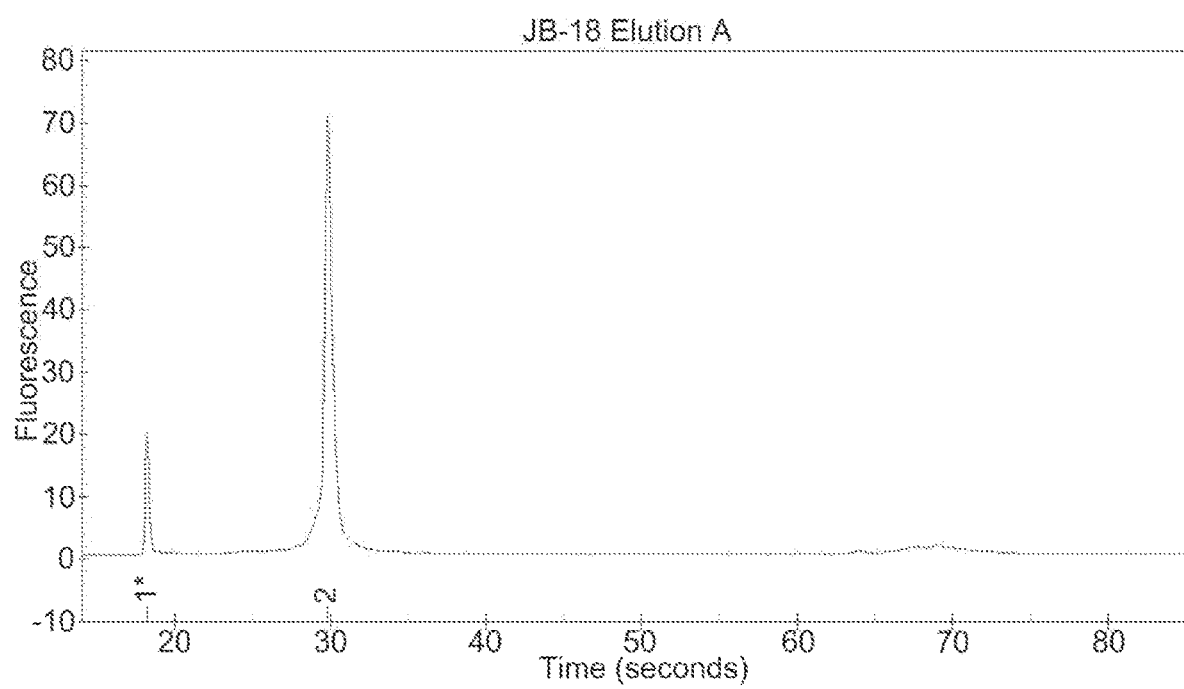
FIG. 3C is an electropherogram of AEX chromatography fractions illustrating AEX purification Elution Pool A, in accordance with an embodiment of the invention
Figure 3D:
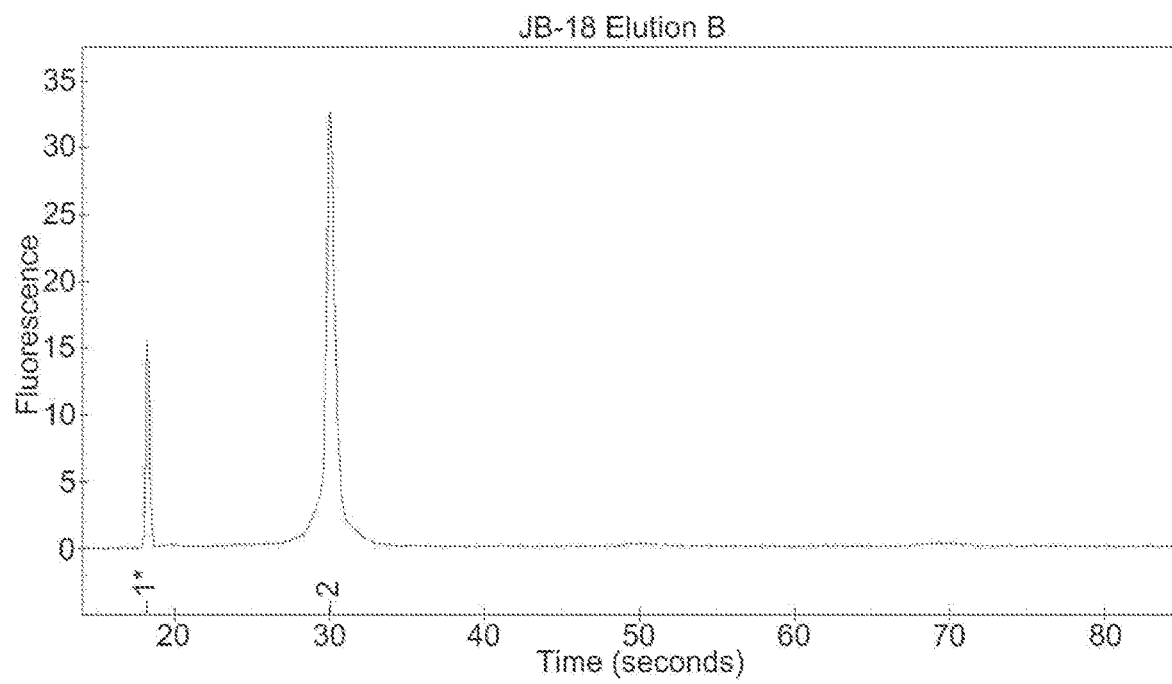
FIG. 3D is an electropherogram of AEX chromatography fractions illustrating AEX purification Elution Pool B, in accordance with an embodiment of the invention FIG. 3E includes overlaid electropherograms of Load Material, Flow Through Pool, Elution Pool A, and Elution Pool B, in accordance with an embodiment of the invention
Figure 3E:
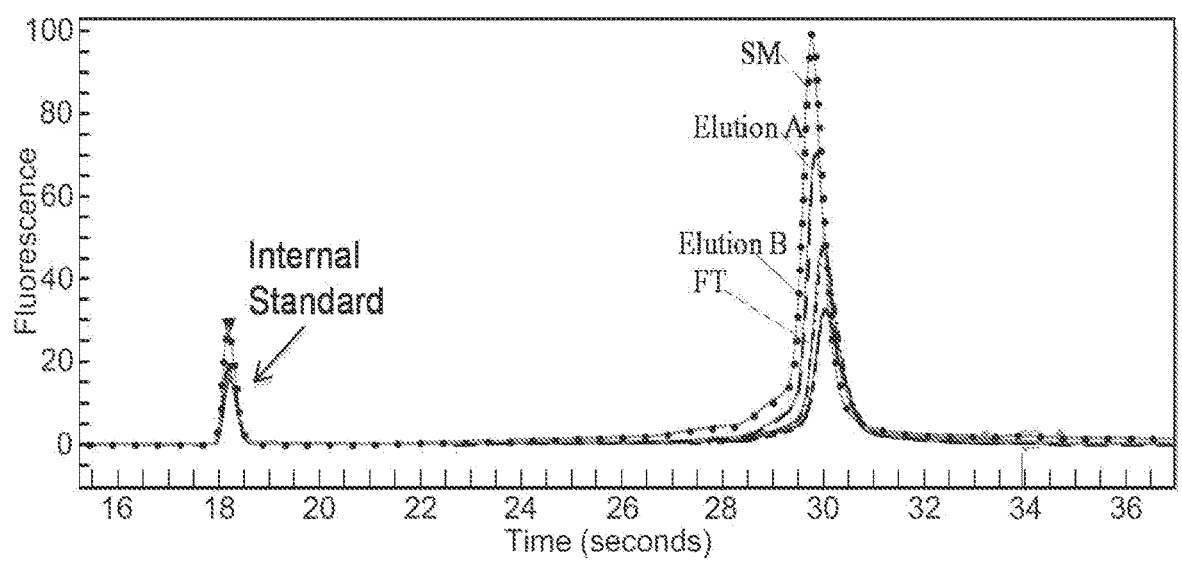

Yield Formula:
Yield = $((C_E \times V_E)/((V_L \times C_L) - (V_{FT} \times C_{FT}))) \times 100$
Dynamic Binding Capacity Formula:
DBC = $((V_L \times C_L) - (V_{FT} \times C_{FT}))/V_C$
DBC = dynamic binding capacity
$C_E$ = concentration of RNA in elution pool
$V_E$ = volume of elution pool
$C_L$ = concentration of RNA in the feedstock
$V_L$ = volume loaded of the feedstock
$C_{FT}$ = concentration of RNA in the flow-through pool
$V_{FT}$ = volume of the flow-through pool
$V_C$ = volume of the column FIG. 3 includes Bioanalyzer electropherograms of AEX chromatography fractions, ~100 ng load per sample. FIG. 3A illustrates GCSF modified mRNA diluted with 2× Sample Buffer (Load Material/Starting Material). FIG. 3B illustrates AEX purification Flow Through Pool. FIG. 3C illustrates AEX purification Elution Pool A. FIG. 3D illustrates AEX purification Elution Pool B. FIG. 3E illustrates overlaid electropherograms of Load Material, Flow Through Pool, Elution Pool A, and Elution Pool B. The similarity in migration times for the main peak in each of the electropherograms in FIG. 3 suggest that the eluted RNA (FIG. 3C and FIG. 3D), after undergoing thermal denaturation, remained structurally similar in both construct size (i.e. number of nucleotides) and conformation to that of the starting material (FIG. 3A). FIG. 3E is a direct comparison of the individual electropherograms; although the peak intensities differ for each of the traces, the migration times for each individual overlaid peak fall within a tight range around the 30 second mark.

Conclusions:

The dynamic binding capacity was observed to be greater than 20 mg/mL (modified mRNA/Sorbent) for this particular sorbent run under the conditions described in the methods section. The combined yield of the three elution pools was calculated to be 86.6% of the amount of theoretical bound material (total material loaded—flowthrough pool). Elevated temperatures do not appear to alter the structural integrity of the modified mRNA as shown in the electropherograms from the bioanalyzer. From this experiment, a binding capacity greater than 20 mg/mL, a product yield greater than 85% combined with evidence of intact RNA after thermal denaturation suggests that this process is viable for use as a preparative technique for RNA separations.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

1. Ketterer L, Von Der Mulbe F, Reidel, L, Mutzke, T. U.S. Pat. No. 8,383,340.
2. Easton L, Shibata Y, Lukaysky P. Rapid, nondenaturing RNA purification using weak anion-exchange fast performance liquid chromatography. *RNA* 2010, 16(3):647-653.
3. Bridonneau P, Bunch S, Tengler R, Hill K. Carter J, Pieken W, Tinnermeier D, Lehrman R, Drolet D W. Purification of a highly modified RNA-aptamer. Effect of complete denaturation during chromatography on product recovery and specific activity. *J Chromatogr B Biomed Sci Appl.* 1999, 726(1-2):237-247.
4. Straus J, Kelly R, Sinsheimer R. Denaturation of RNA with dimethyl sulfoxide. *Biopolymers.* 1968, 6(6):793-807.
5. Lambert D, Draper D E. Denaturation of RNA secondary and tertiary structure by urea: simple unfolded state models and free energy parameters account for measured m-values. *Biochem.* 2012, 51(44):9014-9026.
6. Weissman D, Pardi N, Muramatsu H, Kariko K. HPLC Purification of in vitro transcribed long RNA. *Methods in Molecular Biology.* 2013 969:43-54.
7. Kariko K, Muramatsu H, Ludwig J, Weissman D. Generating the optimal mRNA for therapy: HPLC purification eliminates immune activation and improves translation of nucleoside-modified protein-encoding mRNA. *Nucleic Acids Res.* 2011, 1-10.

What is claimed is:

1. A method for purifying a messenger ribonucleic acid transcript from a sample comprising the messenger ribonucleic acid transcript of 300 to 10,000 nucleotides in length and impurities, comprising the steps of:
    (a) a contacting step comprising contacting the sample to an ion exchange sorbent comprising a positively-charged functional group linked to solid phase media, wherein the sample comprises an aqueous-based solution and the messenger ribonucleic acid transcript binds the positively-charged functional group of the ion exchange sorbent while at least a portion of the impurities in the sample pass through the ion exchange sorbent;
    (b) a washing step comprising washing the ion exchange sorbent with a buffer comprising about 150 mM sodium chloride to cause at least a portion of the remaining impurities to pass through the ion exchange sorbent; and
    (c) an eluting step comprising eluting from the ion exchange sorbent with a buffer comprising about 2 M sodium chloride a purified sample comprising the messenger ribonucleic acid transcript,
    wherein the contacting step, the washing step, and the eluting step are performed at a temperature of about 65 degrees Celsius, and
    at least 80% of the messenger ribonucleic acid transcript in the sample is recovered in the purified sample.
2. The method of claim 1, wherein the messenger ribonucleic acid transcript is a full-length messenger ribonucleic acid transcript.
3. The method of claim 1, wherein the messenger ribonucleic acid transcript comprises nucleosides other than adenosine, guanosine, cytidine, or uridine.
4. The method of claim 1, wherein at least one of the steps comprises a chaotropic agent.
5. The method of claim 4, wherein the chaotropic agent is selected from the group consisting of: perchlorate salts, guanidinium salts, and urea.
6. The method of claim 1, wherein at least one of the steps comprises an organic denaturing agent.
7. The method of claim 6, wherein the organic denaturing agent is selected from the group consisting of: dimethyl sulfoxide (DMSO), acetonitrile, ethanol, and glyoxal.
8. The method of claim 1, further comprising pre-incubating the sample at a temperature of 55 degrees Celsius to 75 degrees Celsius.
9. The method of claim 1, wherein the positively-charged functional group comprises a quaternary amine.
10. The method of claim 1, wherein the impurities are selected from the group consisting of: a fragment of the messenger ribonucleic acid transcript, DNA template, hybridized nucleic acid impurities, enzymes, endotoxins, nucleotides, and small molecules.
11. The method of claim 1, wherein the ion exchange sorbent has a binding capacity of greater than 10 mg messenger ribonucleic acid transcript/mL sorbent.
12. The method of claim 1, wherein the ion exchange sorbent comprises a pore size of greater than 500 Angstroms.
13. The method of claim 1, wherein the ion exchange sorbent is a porous media comprising materials selected from the group consisting of: silica, poly styrene divinylbenzene, polymethacrylate, crosslinked agarose, and allyl dextran with N—N-bis acrylamide.
14. The method of claim 1, wherein the method comprises a column chromatography method.
15. The method of claim 1, wherein the method comprises a batch chromatography method or a chromatography method using a membrane adsorber.

* * * * *